United States Patent [19]
Ritter

[11] Patent Number: 5,219,650
[45] Date of Patent: Jun. 15, 1993

[54] FLEXIBLE SHIELD AGAINST LASER RADIATION

[75] Inventor: Tibor Ritter, San Antonio, Tex.
[73] Assignee: Laser Shields, Great Neck, N.Y.
[21] Appl. No.: 598,038
[22] Filed: Oct. 16, 1990
[51] Int. Cl.⁵ .................................................. B32B 9/00
[52] U.S. Cl. ..................................... 428/323; 428/325; 428/339; 428/340; 428/446; 428/913; 604/369; 604/372
[58] Field of Search .............................. 604/369, 372; 128/132 D, 132 R; 428/323, 325, 446, 339, 340, 913

[56] References Cited

U.S. PATENT DOCUMENTS

| | | | |
|---|---|---|---|
| 3,261,800 | 7/1966 | Collins, III | 523/136 |
| 3,609,372 | 9/1971 | Vogel | 250/518.1 |
| 3,720,836 | 3/1973 | Donges | 250/519.1 |
| 3,895,143 | 7/1975 | Tarlow | 428/40 |
| 4,156,147 | 5/1979 | Naum | 250/515.1 |
| 4,431,697 | 2/1984 | Rolinski et al. | 428/242 |
| 4,520,814 | 6/1985 | Weeks | 606/2 |
| 4,558,093 | 12/1985 | Hatzenbuhler | 524/837 |
| 4,601,286 | 7/1986 | Kaufman | 128/894 |
| 4,604,998 | 8/1986 | Bellina | 128/849 |
| 4,611,588 | 9/1986 | Laptewicz, Jr. | 128/846 |
| 4,657,345 | 4/1987 | Gordon | 252/582 |
| 4,658,812 | 4/1987 | Hatzenbuhler | 128/207.14 |
| 4,715,366 | 12/1987 | Teeple | 128/849 |
| 4,735,623 | 4/1988 | Hazenbuhler | 604/369 |
| 4,901,738 | 2/1990 | Brink | 128/849 |
| 4,980,564 | 12/1990 | Steelman | 428/242 |

*Primary Examiner*—Patrick J. Ryan
*Assistant Examiner*—W. Kryonski
*Attorney, Agent, or Firm*—St.Onge Steward Johnston & Reens

[57] ABSTRACT

A thin flexible shield capable of preventing penetration by full powered medical laser beam is described. The shield is formed with a polymer matrix such as silicone rubber which is loaded with a substantial amount of particulate material. The material is selected to be non-toxic and non-burnable when exposed to a medical laser beam. The particle sizes are selected so as to enhance the ability of the shield to resist burn-through by a medical laser beam. Various materials and particle sizes are described with significant resistance to laser penetration encountered in structures that are as thin as about a millimeter with maximum power focused laser pulses.

20 Claims, 1 Drawing Sheet

FLEXIBLE SHIELD AGAINST LASER RADIATION

FIELD OF THE INVENTION

This invention generally relates to a material for protection against laser radiation and more specifically to flexible drapes capable of protecting against medical laser beams.

BACKGROUND OF THE INVENTION

Plastic compositions for forming barriers against various types of radiation are known in the art. For example, U.S. Pat. No. 3,261,800 proposes a thermoplastic polymer containing from 0.05% to 70% boron nitride to provide a shield against thermal neutrons. U.S. Pat. No. 3,609,372 describes formation of a shaped body as a shield against radioactive radiation such as gamma and neutron radiation. The shield is made with a fatty acid with powdered metals that can be various different types. Other U.S. patents describing various compositions for shielding are U.S. Pat. No. 3,895,143 which proposes various powdered metals or oxides or sulfides in a latex 20 matrix to provide protection against radar, x-rays, radioactive and television radiations; and U.S. Pat. No. 4,156,147 which describes a neutron absorbing plate that uses boron carbide and silicon carbide particles.

Medical laser beams are usually characterized by focusing a large amount of radiation in a very small spot. Typically, a beam of about 20 to about 50 watts is focused to a very small area (about 0.03 mm$^2$) so as to create a high power density (optical power per unit area) sufficient for cutting or cauterizing. The medical laser beam may be pulsed or continuous depending upon the desired mode of operation.

Medical laser beams usually have a focal point about three centimeters or less from the tip of the hand-held instrument. Beyond this focal point, the laser beam again diverges. However, the intensity of the divergent beam is still sufficient to cause eye damage and skin damage at considerable distances from the instrument. For example, the anesthesiologist is often seated behind a drape, which serves as a sterile screen. This screen, however, offers little or no protection against the laser beam. The beam is sufficiently intense to penetrate a typical paper or cloth drape and injure persons behind it. Accordingly, great care should be taken to protect the various personnel in an operating room as well as the patient against inadvertent and random oriented laser beams activations.

Various laser protection devices have been proposed. One technique frequently relied upon for the patient is a series of wet sponges surrounding the site where the surgeon needs to work. It has been found, however, that the very laser, typically a $CO_2$ laser, used to work on a patient because its wavelength is absorbed by moist flesh, also is absorbed by the moist sponge. This absorption quickly allows the beam to form a narrow column of evaporated moisture in the sponge to then expose underlying skin to almost the full intensity of the beam. The protection of the moist sponge is, therefore, not normally sufficient against a medical laser beam.

Other U.S. patents related to laser shields employ powder in a polymer mix, U.S. Pat. No. 4,611,588; or powdered aluminum in a polymer matrix such as rubber latex, U.S. Pat. No. 4,520,814. In U.S. Pat. Nos. 4,604,998, 4,715,366 and 4,901,738, laser shields are described using metal foils such as formed of aluminum. This foil can be covered by a non-reflective surface. But when this is impacted by a medical laser beam, it tends to be quickly penetrated so that the underlying foil reflects the beam in a random, often dangerous, direction. U.S. Pat. No. 4,658,812 describes a laser shield formed of tiny glass bubbles whose sizes are in the range from 20 to 200 microns and are imbedded with or without water in a silicone matrix. Glass has a fusion temperature of the order of about 800° C. and this tends to melt rather quickly when exposed to a highly powered focused laser beam.

Graphite and certain metal powders have been found to be prone to burst into flame or eject small burning particles when exposed to a high intensity medical laser beam. Burnable or readily oxidizable materials are, therefore, dangerous to a patient and personnel in an operating room. The resistance of metal foils to penetration often is inadequate when a medical laser inadvertently impacts a metal foil at full focused power for a short instance. Reflective shields, furthermore, can reflect the beam to some other spot without sufficient attenuation and consequently, only redirect the beam for damage to be caused elsewhere.

Although resistance to laser penetration is enhanced by increasing the thickness of a barrier, such improved resistance impairs the flexibility of the barrier and its ability to properly drape around a patient and personnel.

SUMMARY OF THE INVENTION

With a composition in accordance with the invention, a shield is provided capable of withstanding high power impacts from medical lasers for extended times while protecting persons from the laser beam in a safe manner.

This is achieved in accordance with one technique in accordance with the invention by forming a flexible, relatively thin structure which is highly loaded with generally uniformly distributed, laser blocking particles that are captured in a flexible matrix, and wherein the particles are formed of a non-toxic material which does not burn or tend to violently oxidize or undergo other violent reactions when impacted by a fully powered medical laser beam and wherein the particles are formed of a material and have a size selected to enhance scattering of the medical laser beam within the structure so as to resist penetration by the laser beam.

With a laser beam resistant structure in accordance with the invention, the particles preferably are formed of a material which undergoes a change in phase from a solid state at a high temperature and have a size selected to promote scattering of an incident laser beam. The materials effective for this can be of the refractory type or other high melting or sublimation temperature materials which do not readily oxidize, are non-toxic and non-carcinogenic and safe when melted or evaporated by the incidence of a medical laser beam. The particle sizes of these materials further are selected so that a medical laser beam is unlikely to tunnel through the structure but tends to be scattered internally so as to render penetration difficult even when the structure is thin.

With a laser beam resistant structure in accordance with the invention, an effective flexible and thin laser shield is obtained capable of withstanding a large number of maximum powered laser pulses or continuous beam power for a sufficient length of time without penetration and without dangerous reflections.

It is, therefore, an object of the invention to provide a medical laser shield structure that is flexible, easily drapable and capable of safely resisting prolonged exposure to a full powered medical laser beam without penetration by the beam.

These and other advantages and objects of the invention can be understood from the following detailed description of the invention in conjunction with the drawing.

BRIEF DESCRIPTION OF DRAWINGS

The Figure is a greatly enlarged partial crossectional view of a preferred form of the invention.

DETAILED DESCRIPTION OF DRAWINGS

Figure 1:
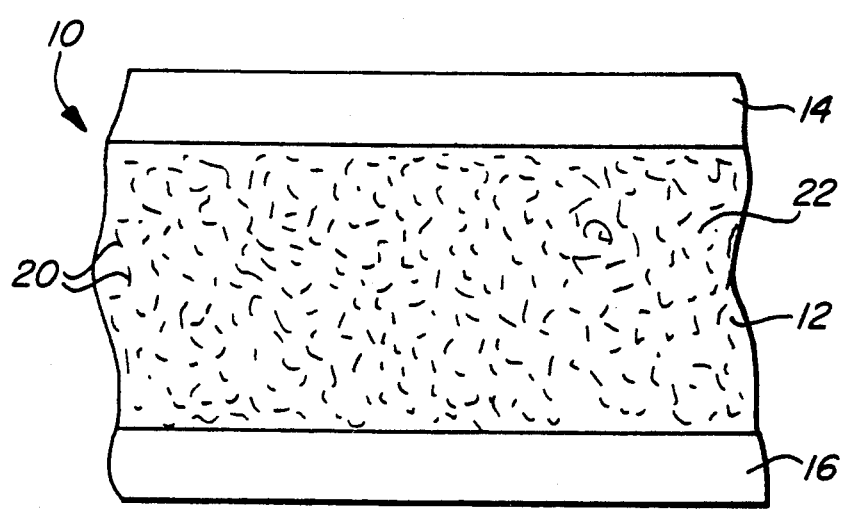

In the Figure a thin structure 10 that is part of a laser shield sheet is shown. The structure is laminated and formed of an inner layer 12 bounded on both sides by thin flexible outer layers 14, 16 that can be paper or thin cloth or such other suitable sterile flexible material that can adhere to the inner layer 12 either with an adhesive or by way of a natural affinity with inner layer 12. Other lamination techniques as are well know in the art can be used to adhere the layers.

Inner layer 12 is formed of a polymer matrix 18 throughout which a substantial loading of inorganic laser blocking particles 20 are distributed. The particles are formed of a material that undergoes a phase change from a solid phase at a high melting point or sublimation point, at least above about 1,000° C., and that does not readily burn when exposed to a full powered, focused medical laser beam and is non-toxic, non- carcinogenic and safe when a patient or operating room personnel are exposed to its melted or vaporized form in the amounts as may be melted or vaporized in accidental beam impacts.

The amount of particles 20 distributed throughout layer 12 is selected so that the polymer matrix is highly loaded. The amount of particles should be selected sufficient to present a highly obstructed path for an incident laser beam yet not in such high quantity as to significantly degrade the flexibility and drapability of the layer 12 and to render the layer excessively crumbly. An excessive loading further should be avoided to minimize chances of the separation of individual particles from the structure and lodging in or near surgical openings.

Loading of particles 20 should thus be at least about 30% by weight of layer 12 but not greater than about 90%. Preferably, the loading with particles 20 should be in the range from about 75% to about 85% with good laser resistance found at the high loading end where some samples appeared crumbly.

Another consideration of the amount of loading depends upon the method of manufacture. For example, if an extrusion technique is relied upon to lay down layer 12, a high loading of particles 12 may be difficult to handle and lower loadings adopted.

The sizes of particles 20 have been found to be a factor in the effectiveness of layer 12 in resisting penetration of a medical laser beam. Generally, the larger the individual blocking particles 20 within a range, the more effective the laser shield 10 tends to be. Mesh sizes for particles, therefore, are further selected to enhance laser beam resistance, yet not so large as to render the composition difficult to handle during manufacture. Generally, particle sizes are selected so as to be not much smaller than about 300 mesh and preferably are larger than about 220 mesh. Particles of about 100 mesh yielded good laser resistance while particles 20 that are larger than about 47 mesh, though performing acceptably, tended to introduce an unevenness in the thickness of layer 12. Particle sizes may be as large as about 30 mesh.

The polymer matrix 22 through which the blocking particles are distributed can be formed of a broad range of materials provided these do not tend to yield unsafe fumes or substances when exposed to a full powered laser beam. Various types of polymer matrices that can be used are extensively described in the art such as plastic or rubber. However, a particularly effective polymer matrix is silicone rubber.

The laser blocking particles 20 can be selected from various non-combustible materials. Refractory particles, such as made of silicone carbide or alumina, have been found effective.

EXAMPLE 1

A mixture was made of a two part (A & B) silicone polymer matrix made by Dow Chemical and known as Dow Corning Silicone Rubber 591 in the amount of 5 grams of each for A and B components and 20 grams of a naphta solvent known as Varnishmakers and Painters (VM&P) naphta and made among others by Union Oil Co., Shell Chemical Co. or Texaco Chemical Co., distributed among others by E. E. Zimmerman Co., Pattsburgh, Pennsylvania 15233. Silicon carbide laser blocking particles manufactured by The Norton Co., Worchester, Massachusetts under the name "Crystolon" were added of two different particle sizes, one of which was 220 mesh (about 70 microns) and the other 100 mesh (149 microns). In each case, 50 grams of laser blocking silicon carbide particles were added and the entire mixture thoroughly blended.

Note that other silicone rubbers can be used such as Dow Corning 590 and 595.

The mixtures were then spread over a portion of a bottom drape formed of a commercially available non-woven, single use surgical drape, such as sold by the Hospital Supply Division of the Baxter Health Care Corp. to form even coatings and allowed to dry so that the naphta solvent evaporated to leave a dry laser blocking structure.

A top drape portion was coated with a combination of equal amounts of the A and B silicone polymer matrix and this drape portion was placed on the dried blocking structure and allowed to dry for several hours. After this drying, the laminated laser blocking structure was heated in an oven at 275° F. until cured for about 10 minutes.

The two samples had a thickness as set forth in Table I below and were tested with a medical $CO_2$ laser at full power, 50 watts both with 0.2 second long pulses and at a continuous power setting. The laser testing was done with the samples at the focal point of the medical laser beam, i.e., at a focal distance of 1 cm.

TABLE I

| Sample | Thickness | Number of Pulses Needed To Penetrate Sample | Duration of Continuous Beam To Penetrate Sample |
| --- | --- | --- | --- |
| 220 mesh | .15 inch | 10 | 1.75 sec (est) |
| 100 mesh | .135 inch | more than 10 | 1.75 sec |

One problem associated with laser shields is how to evaluate their performance and what standards should then be applied to determine their effectiveness. The prior art is not consistent in its approach. For example, in the U.S. Pat. No. 3,720,836 a $CO_2$ laser is used at a setting of a 100 watts with a focal area 1 mm diameter or 12.74 KW/cm continuous power. Neither U.S. Pat. No. 4,611,588 nor 4,658,812 identify any power density. U.S. Pat. No. 4,901,738 identified flamability problems with drapes exposed to laser powers from 10 to 40 watts and beam widths from 0.6 to 5.8 mm. but tested foils at 5 watts with 2 mm beams (159 watts/cm) and tested samples with a laser beam intensity of about 16 KW/cm and at about 64 KW/cm². The underlying aluminum foil tends to be exposed in each case after short bursts of as little as a half second.

Typically, medical laser beam generating systems have three operating modes. A continuous power mode, a pulsed mode with a maximum pulse duration typically of about 0.2 seconds and a super pulsed mode in which a very high peak power occurs in a very short pulse of the order of 10 milliseconds. In many medical laser operations, a machine burst mode is possible in the super pulse mode during which a large number of pulses are produced as long as a foot pedal is actuated.

In typical medical applications where cauterizing is needed, a relatively low power setting is needed, i.e., usually below about 1 KW/cm. When cutting is needed, the power setting is increased to maximum, the focal spot reduced (usually by replacing the tip lens) to create power densities in the range of 150 KW/cm². In a medical laser beam, this can be achieved in the vicinity or at the focal point, whose diameter is about 0.2 mm., with a maximum power setting of 50 watts. In endotracheal procedures, lower laser power settings, of the order of 10 watts are used, but protective laser shield capability by an endotracheal tube is still desirable.

The situations for which a laser shield is needed occur when a laser beam is mis-aimed or is inadvertently activated while randomly aimed. This means the shield can be at the focal point or beyond it. Typically, this inadvertent operation is quickly realized, but seconds of physical protection are needed.

By testing of the materials with the medical laser at its potentially most dangerous condition, the effectiveness of the laser blocking composition can be estimated. Hence, the standard adopted for laser shields in accordance with the invention requires that for a given thickness and flexibility they be capable of stopping, without substantial or significant reflection, the full or maximum focused power of a medical laser beam for a time period that is at least from about one to about three seconds at continuous or pulsed power. In the case of a pulsed medical laser beam, this means at least five pulses of 0.2 seconds with a repetition rate of two pulses per second for a sample that is drapable and flexible and has a thickness of about 0.125 inches (about 3.2 mm). For thinner drapes, as may be used at sites remote from the operating area and which are potentially exposed only to unfocused beams, a lower power density test causing penetration at shorter exposures can be tolerated.

The formation of a laser shield in accordance with the invention may also be done by extruding a blend such as described in Example 1 on a non-adhesive release surface, such as formed of Teflon (a trademark of DuPont Company). Following heat curing of the dried structure, it is coated on both sides with the same silicone polymer mixture which contains no added laser blocking material. The thickness of the resulting laser can be from about 0.010 to about 0.3 inches thick, depending upon the desired flexibility and the extent of laser penetration resistance that is required.

Heavier or thicker coatings may be made by reducing the solvent. The silicone carbide mixture can also be prepared without a solvent by extruding and curing using conventional silicone rubber processing equipment. Top and bottom covering of the shield by drape fabrics or by unfilled silicone rubber layers can be combined with the extrusion procedure, if desired or may be carried out as a subsequent series of manufacturing steps.

The laser shield composition may also be extruded as a tubing (with coincident or subsequent coating) for use as endotracheal tubular laser shields.

Various loadings of the laser blocking particles were investigated. It was found that for good laser blocking, the loadings should be substantial, generally at least about 30% by weight of the cured composition and preferably above about 75% with good performance with loadings up to about 84%. With higher loadings, the initial mixture becomes stiffer and harder to draw into a smooth layer.

During an investigation using different laser blocking particles, it was discovered that particle mesh sizes were a factor in the effectiveness of the laserblocking composition. Generally, the finer or smaller the particles, the more easily a full powered medical laser beam could penetrate This is illustrated by Table II in which silicon carbide compositions and one silicon dioxide composition were made with RTV silicone rubber or with the two-part silicone rubber used in Example I as noted. It is believed that the use of larger particles enhances the internal scattering of a laser beam, thus spreading its heating effect to other larger particles and thus inhibit laser penetration.

TABLE II

| Loading 83% Mesh Size | Layer Thickness Inches | Focused Laser Pulses At 50 W .2 Seconds To Burn-Through |
|---|---|---|
| Silicon Carbide: | | |
| 600 | .125 | 1 |
| 320 | .125 | 2 |
| 220 | .125 | 6 |
| 100 | .125 | 7 |
| 100 (2 part silicone) | .110 | 24 |
| 46 | .150 (uneven) | 6 |
| Silicon Dioxide: | | |
| 320 | .125 | 1 |
| 60–200 (2 part silicone) | .104 | 20 |

Although increasing thickness can be expected to improve the laser blocking capability of the composition, the effectiveness of various laser blocking materials at 80% loading in practically thin layers was investigated as shown in Table III using the two-part silicone rubber of Example 1.

TABLE III

| Laser Blocker Particle Size 80% Loading Unless Otherwise Noted | Thickness | Focused Laser Pulses At 50 W. .2 Seconds To Burn-Through |
|---|---|---|
| Silicon Carbide: | | |
| 100 mesh | .035 | 6 |
| 100 mesh | .066 | 7 |
| 100 mesh | .091 | 18 |
| 100 mesh | .110 | 24 |

TABLE III-continued

| Laser Blocker Particle Size 80% Loading Unless Otherwise Noted | Thickness | Focused Laser Pulses At 50 W. .2 Seconds To Burn-Through |
|---|---|---|
| 100 mesh @ 84.6% loading | .104–.125 | *more than 20 |
| 100 mesh | .13–.14 | *more than 20 |
| 220 mesh | .12–.14 | *more than 20 |
| 100 mesh | **.2–.22 | *more than 20 |
| Silicon Dioxide: | | |
| 320 mesh | .037 | 2 |
| 60–200 mesh | .050 | 2 |
| 60–200 mesh | .091 | 13 |
| 60–200 mesh | .104 | 20 |
| Aluminum Oxide: | | |
| 100 mesh | .044 | 5 |
| 100 mesh | .066 | 7 |
| 100 mesh | .091 | 14 |

*These samples also withstood penetration when exposed to continuous 50 watt medical laser power at the focal distance.
**This sample was stiffer but still flexible.

The laser blocker material should have a sufficiently high melting or sublimation temperature to enable it to effectively function within a drape. Melting points of 561° C. and 800° C. were found too low so that a fully powered medical laser would penetrate a 0.11 inch thick sample with a single pulse. Laser blocker materials whose phase change from a solid occurs at a substantially higher melting point should be used, at least above 1000° C. and preferably at least above 1700° C. as encountered with silica, alumina and silicon carbide.

Having thus described several embodiments for a laser blocking composition in accordance with the invention, its advantages can be appreciated. Relatively thin flexible structures can be formed capable of resisting high laser power without penetration, without burning to provide a safe environment for the patient and attending operating personnel. Other forms such as tubular shapes can be made.

What is claimed is:

1. A laser beam resistant composition for use in medical applications and capable of withstanding the impact of a highly powered medical laser beam without burn-through, comprising:
   a flexible, relatively thin structure loaded with a substantial amount of generally uniformly distributed material particles captured within a flexible matrix, wherein the particles are formed on a non-toxic material which is non-burnable when exposed to a medical laser beam and undergoes a phase change from a solid state at a sufficiently high temperature so as to resist penetration of the structure by a medical laser beam for at least a desirable time interval and wherein the material particles have a size in the range from about 300 mesh to about 30 mesh to enhance the ability of the structure to resist burn-through by a medical laser beam.

2. The laser beam resistant composition as claimed in claim 1 wherein the material particles are selected so as to be generally larger than about 300 mesh.

3. The laser beam resistant composition as claimed in claim 2 wherein the material particles are selected so as to be generally larger than about 250 mesh.

4. The laser beam resistant composition as claimed in claim 3 wherein the material particles are selected so as to be generally larger than about 100 mesh.

5. The laser beam resistant composition as claimed in claim 1 wherein the material is selected from the group consisting of silicon carbide, alumina and silica.

6. The laser beam resistant composition as claimed in claim 1 wherein the material is a refractory material.

7. The laser beam resistant composition as claimed in claim 1 wherein the structure contains material particles in excess of about 30% by weight of the structure.

8. The laser beam resistant composition as claimed in claim 7 wherein the structure contains material particles in excess of about 75% by weight of the structure.

9. The laser beam resistant composition as claimed in claim 8 wherein the structure contains material particles in an amount that is in the range from about 75% to about 90% by weight of the structure.

10. A laser beam resistant composition for use in medical applications and capable of withstanding the impact of a highly powered medical laser beam without burn-through, comprising:
    a flexible effectively non-laser-beam-reflective structure having a thickness in the range from about 0.035 inches to about 0.2 inches (5.1 mm) and formed of a polymer matrix which is loaded with a substantial amount of material particles of at least 30% by weight of the structure and wherein the material particles have a size selected to be larger than about 300 mesh and smaller than about 30 mesh, said sizes being selected and said particles being further formed of a material whose phase transition temperature from a solid state is at least above about 1700° C. so as to enhance the ability of the structure to effectively resist burn-through by a full power focused medical laser beam.

11. The laser beam resistant composition as claimed in claim 10 wherein the amount of said material particles is in the range from about 60% to about 90% by weight of the structure.

12. The laser beam resistant composition as claimed in claim 10 wherein the amount of said material particles is in the range from about 75% to about 90% by weight of the structure.

13. The laser beam resistant composition as claimed in claim 11 and further including upper and lower cover layers laminated to the polymer matrix layer respectively.

14. The laser beam resistant composition as claimed in claim 11 wherein the sizes of the material particles are selected to lie generally within the range from about 250 mesh to about 30 mesh.

15. The laser beam resistant composition as claimed in claim 14 wherein the particles are made of a refractory material.

16. A laser beam resistant composition for use in medical applications and capable of withstanding the impact of a focused, high-power medial laser beam without burn-through, comprising:
    a flexible, relatively thin structure formed with a flexible matrix which is loaded with a substantial amount of distributed laser blocking particles captured within the flexible matrix, said particles being formed of a non-toxic material which does not burn and resist violent oxidation when impacted by a fully-powered medical laser beam; said particles being of a size in the range from about 300 mesh to about 30 mesh and being formed of a material which undergoes a change of phase at a sufficiently high temperature, so as to enhance scattering of the medical laser beam within the thin structure to impart resistance to the thin structure to penetration by a medical laser beam.

17. The laser beam resistant composition as claimed in claim 16 wherein the loading of particles within the structure is sufficiently high to present particle obstructed paths for an incident medical laser beam and sufficiently low to avoid a significant degradation in the flexibility of the structure.

18. The laser beam resistant composition as claimed in claim 17 wherein the loading of said particles is in the range from about 30% to about 90% of the weight of the structure.

19. The laser beam resistant composition as claimed in claim 18 wherein the loading of said particles is in the range from about 75% to about 85% of the weight of the structure.

20. The laser beam resistant composition as claimed in claim 1 wherein the loading of particles within the structure being sufficiently high to present particle obstructed paths for an incident medial laser beam and sufficiently low to avoid a significant degradation in the flexibility of the structure.

* * * * *